United States Patent [19]

Spaziante et al.

[11] 4,281,184

[45] Jul. 28, 1981

[54] MONOCHLOROACETIC ACID PROCESS

[75] Inventors: Placido Spaziante, Lugano, Switzerland; Giancarlo Sioli, Cernobbio; Luigi Giuffre, Milan, both of Italy

[73] Assignee: Fondazione deNora, Milan, Italy

[21] Appl. No.: 888,954

[22] Filed: Mar. 22, 1978

[30] Foreign Application Priority Data

Feb. 16, 1978 [IT] Italy .............................. 20313 A/78

[51] Int. Cl.³ ........................................... C07C 51/363
[52] U.S. Cl. ................................ 562/603; 260/544 L; 562/607
[58] Field of Search ........................................ 562/603

[56] References Cited

U.S. PATENT DOCUMENTS 3,576,860  4/1971  Zazaris ................................. 562/603

Primary Examiner—Jane S. Myers
Attorney, Agent, or Firm—Hammond & Littell, Weissenberger and Muserlian

[57] ABSTRACT

Production of monochloroacetic acid with a minimum of polychlorinated derivatives in a two stage process by reaction of acetic anhydride and hydrogen chloride at a low temperature to produce a solution of acetyl chloride in acetic acid and chlorinating the said solution at a higher temperature which may be effected in a continuous manner.

5 Claims, 1 Drawing Figure

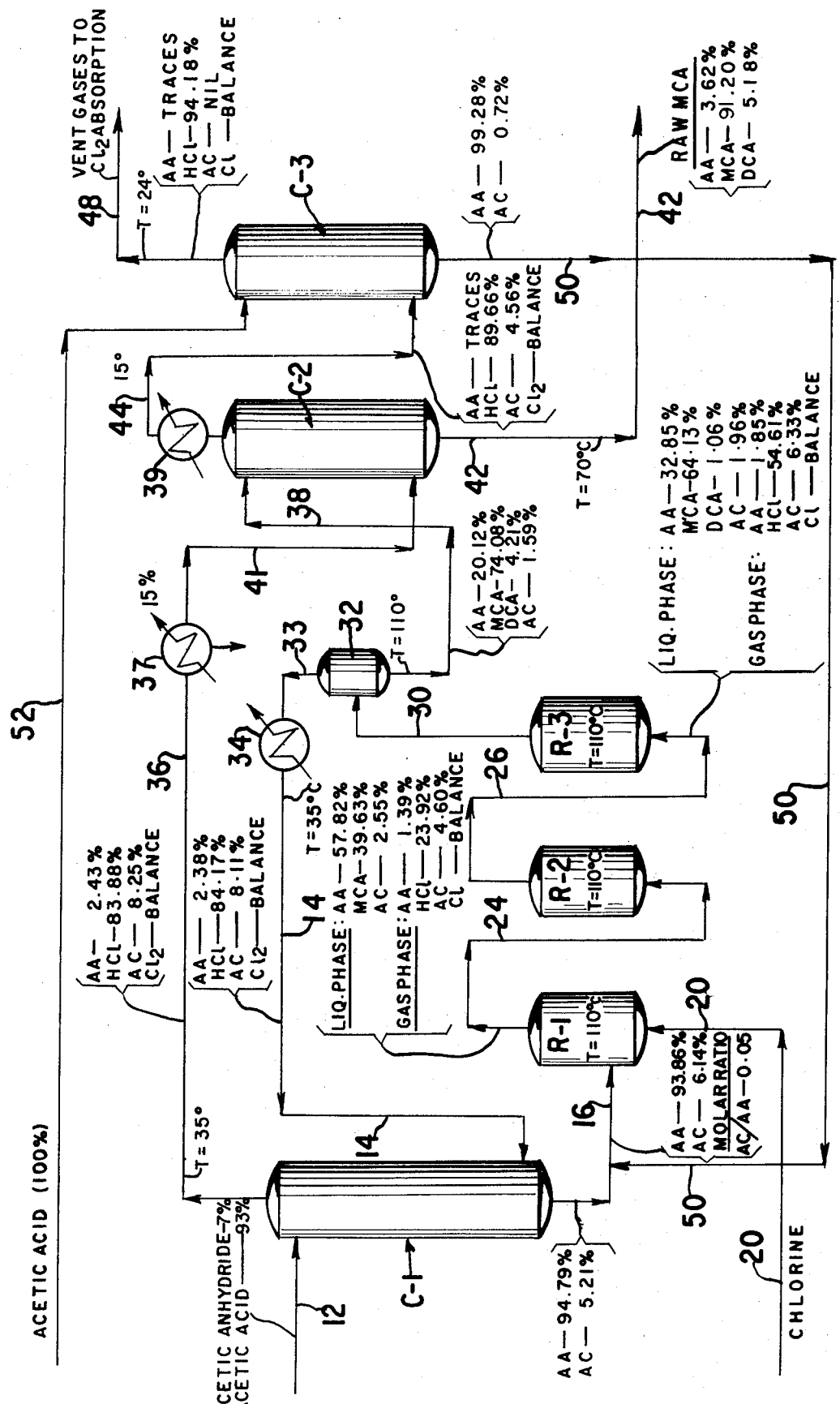

've4,281,184

MONOCHLOROACETIC ACID PROCESS

STATE OF THE ART

The production of monochloroacetic acid by reaction of elemental chlorine and acetic acid is known. For instance, U.S. Pat. No. 2,539,238 describes a process in which acetic acid and acetic anhydride are chlorinated under various conditions. U.S. Pat. No. 2,688,634 discloses the reaction of acetic acid with chlorine in the presence of acetyl chloride or acetic anhydride. The processes disclosed are normally batch processes which usually entail periodic opening of a reactor and exposing personnel to the fumes coming therefrom which are toxic. Also, difficulty is encountered in avoiding loss of highly volatile by-products such as acetyl chloride and avoiding overchlorination to produce polychloroacetic acid.

OBJECTS OF THE INVENTION

It is an object of the invention to provide a novel process for the production of monochloroacetic acid with a minimum of polychlorinated impurities.

It is another object of the invention to provide a two stage process for the production of monochloroacetic acid in good yields with a minimum amount of acetic anhydride catalyst.

It is a further object of the invention to provide a continuous process for producing monochloroacetic acid without exposing personnel to dangerous fumes and with a minimum loss of acetyl chloride and other volatile products.

These and other objects and advantages of the invention will become obvious from the following detailed description.

THE INVENTION

The novel process of the invention is conducted in two separate and distinct stages and in the first stage, a mixture of acetic acid and acetic anhydride is contacted with hydrogen chloride, preferably in the form of a gas comprising hydrogen chloride which may contain some amount of acetyl chloride and chlorine in small amounts. This step achieves a reaction of hydrogen chloride with acetic anhydride producing acetyl chloride and preferably, the reaction is conducted at a low temperature, usually below 60° C. and generally at 35° C. or below, preferably at or below 25° C. but not less than the freezing point of acetic acid so that the resulting acetyl chloride largely or entirely remains dissolved in the acetic acid. The conversion of acetic anhydride to acetyl chloride is normally very high and usually approaches 100%. However, lower conversion ratios may be tolerated.

In the second and separate step which is generally remote from the first step, the resulting mixture of acetic acid and acetyl chloride is subjected to chlorination, usually at a temperature at least 10° C. above the temperature of the reaction of Step 1 and generally above 60° C., and usually at a temperature of 75° to 150° C. preferably about 90° to 120° C. The amount of chlorine supplied is rarely in excess of that amount which is theoretically required to convert the incoming acetic acid to monochloroacetic acid and preferably, the amount of chlorine fed to the chlorination zone is below about 85% of this amount. To achieve relatively high reaction rates, however, at least 65% of such theoretical amount of chlorine should be introduced.

Summarizing, a concentration of acetyl chloride is established in acetic acid by reacting hydrogen chloride with acetic anhydride before or at least separate from the chlorination step, preferably at a relatively low temperature, and this mixture is separately reacted with chlorine advantageously at a higher temperature. This process is most effectively conducted in a continuous cyclic operation wherein acetyl chloride is recycled to minimize losses and the process is broken down into a series of individual steps with the respective conditions of each operation being adjusted to those which are optimum for that particular step.

For example, the reaction of chlorine with acetic acid and acetyl chloride occurs more readily at an elevated temperature above 60° C. as discussed above. This elevated temperature which rarely exceeds 150° C. can be established by exothermic heat of the chlorination reaction with cooling if necessary. On the other hand, if hydrogen chloride is contacted with acetic anhydride at an excessive temperature, the resulting acetyl chloride is volatilized and may have to be recovered by condensation. Also if the temperature is too high, undesirable by-products may be formed. Therefore, this reaction is better conducted at the lower temperature specified above. Even at such low temperatures, if excess hydrogen chloride is used, some acetyl chloride may escape with the escaping hydrogen chloride. However, this may be at least partially recovered by condensation and/or by scrubbing with cold acetic acid and the resulting acetyl chloride-acetic acid solution is forwarded to the chlorination reaction.

The accompanying drawing is a flow sheet which diagrammatically illustrates a cyclic method of performing the process of the invention. All percentages set forth therein as well as those mentioned hereinafter are by weight unless expressly stated otherwise.

As shown in the drawing, a mixture containing 7% acetic anhydride and 93% of acetic acid (glacial) is fed at room temperature continuously through line 12 into the top of a packed glass-lined, polytetrafluoroethylene or graphite-lined gas-liquid contact Column C-1 and flows down over the packing (or through bubble plates) countercurrent to an upwardly rising continuous stream of hydrogen chloride gas which enters the column at the bottom thereof from line 14. This gas also may contain acetic acid, acetyl chloride and some chlorine.

The temperature of the column C-1 or at least the top thereof is held low enough to minimize the escape of acetyl chloride, for example at about 35° C. or below, and thus acetic anhydride reacts with the hydrogen chloride and forms acetyl chloride thereby producing a liquid mixture of acetic acid-acetyl chloride which is essentially water free.

Since the hydrogen chloride stream fed to line 14 conveniently comes originally from the monochloracetic acid reaction, it has the following composition in gaseous state:

Acetic Acid (AA): 2.38% percent by weight;
Hydrogen Chloride: 84.17% percent by weight;
Acetyl Chloride (AC): 8.11% percent by weight;
Chlorine: Balance.

The height of the column C-1 and the depth of the packing therein is great enough to convert all of the acetic anhydride to acetyl chloride.

The amount of hydrogen chloride passing through the column C-1 is considerably in excess of that amount of hydrogen chloride required to convert the acetic anhydride to acetyl chloride, generally being 100 to 1000 mol percent of more in excess of that amount. The off gas from column C-1 may contain substantial acetyl chloride which may be scrubbed with cold acetic acid and the recovered acetyl chloride-acetic acid solution is sent to the chlorination stage as discussed below.

A liquid mixture of 94.79% of acetic acid and 5.21% of acetyl chloride is withdrawn from the lower part of column C-1 through line 16 and is mixed with a recycling stream coming from line 50 containing about 99.28% of acetic acid and about 0.72% of acetyl chloride to produce a mixture containing 93.86% acetic acid and about 6.14% of acetyl chloride. Thus, the molecular ratio of acetyl chloride to acetic acid therein is about 0.05.

This mixture is fed continuously through line 16 and gaseous elemental chlorine is fed through line 20 into the bottom of reactor R-1 and, as diagrammatically illustrated, the mixture of gas and liquid reactants and reaction products flow concurrently and successively from reactor to reactor through a series of reactors R-1, R-2 and R-3. Reactors R-2 and R-3 are connected to reactor R-1 and R-2 through exit lines 24 and 26, respectively. These lines lead from the top of one reactor to the bottom of the next succeeding reactor in the series with chlorine, acetic acid and acetyl chloride being maintained in the reaction mixture by thorough mixing while the reaction is under way.

The composition of the respective gas and liquid phases flowing through the respective lines are as follows:

|  | Line 24 to Reactor R-2 | | Line 26 to Reactor R-3 | |
| --- | --- | --- | --- | --- |
|  | Gas Phase | Liquid Phase | Gas Phase | Liquid Phase |
| Acetic Acid (AA) | 1.39% | 57.82 | 1.85% | 32.85 |
| Monochloroacetic Acid (MCA) | trace | 39.63 | trace | 64.13 |
| Acetyl Chloride | 4.60% | 2.55 | 6.33 | 1.96 |
| Chlorine | Balance | trace | Balance | trace |
| Hydrogen Chloride | 23.92% | trace | 54.61 | trace |
| Dichloroacetic Acid | Nil | Nil | Nil | 1.06 |

Temperature in the reactors is maintained by cooling the reaction mixture to absorb heat of chlorination and to hold the temperature at a suitable level of about 90° to 120° C., for example at 110° C., and the liquid reactants and reaction mixtures are stirred to avoid channeling. The total retention time of the reactants in the reactors is about 3 to 8 hours.

The reactors may be of any convenient construction such as a jacketed glass-lined kettle provided with a stirrer. The reactors are largely filled with the liquid phase reactants and the chlorine or gas phases are intimately mixed with the liquid phases.

Ultimately, the reaction mixture flows from the top of reactor R-3 through line 30 to a phase splitter 32 which separates the liquid phase from the gas phase.

This gas is fed through line 33 to a cooler 34 where it is cooled to about 35° C. or below and then fed through line 14 to the bottom of column C-1. Therefore, this gas constitutes the hydrogen chloride gas which was referred to above as flowing counter-currently to an acetic acid-acetic anhydride mixture in column C-1. The temperature of the column C-1 is held at or below about 35° C. and as stated above acetyl chloride is generated therein.

Gas or vapor escaping from the top of the column C-1 has the following compositions:
Acetic Acid: 2.43 Percent;
Hydrogen Chloride: 83.88 Percent;
Acetyl Chloride: 8.25 Percent;
Chlorine: Balance.

The gas leaves column C-1 at a temperature of about 35° C. through line 36 and is further cooled to about 15° C. by passing through cooler 37. After cooling, the cooled gas is sent through line 41 to the lower part of column C-2. Condensate of acetic acid and acetyl chloride from cooler 37 is transferred by means not shown to one of the reactors R-1, R-2 or R-3.

The liquid phase from phase splitter 32 has the following composition:
Acetic Acid: 20.12 Percent;
Monochloroacetic Acid: 74.08 Percent;
Di Chloroacetic Acid: 4.21 Percent;
Acetyl Chloride: 1.59 Percent.

This liquid phase is delivered to the upper portion of packed column C-2 through line 38 and thus flows counter current to the incoming hydrogen chloride delivered through line 41. The temperature of the liquid is at reaction temperature of the reactor or, in this example, about 110° C. The gas exits from the top of column C-2 at a temperature of 90° C. and is cooled by passing through a condenser-cooler 39 to a temperature of about 15° C. The liquid escaping from the bottom through line 42 has a temperature of about 155° C. and this is the crude monochloroacetic acid product which is to be purified by crystallization or other means to separate monochloroacetic acid from unreacted acetic acid and polychloroacetic acids.

The effect of the counter current gas-liquid contact in column C-2 is to strip acetyl chloride from the liquid phase so that the raw product contains little or no acetyl chloride. Also, some acetic acid is removed from the gas phase by condensor 39 and is recycled to preferably reactor $R_1$ by means not shown. Thus the gas phase escaping through line 44 from the top of the column has the composition:
Acetic Acid: Trace;
Hydrogen Chloride: 89.66;
Acetyl Chloride: 4.56;
Chlorine: Balance.

This gas phase is delivered by line 44 to the bottom of packed column C-3 where it is counter currently scrubbed with cold liquid glacial acetic acid by line 52 to remove acetyl chloride therefrom. The gas leaving the top of the column C-3 through line 48 has a temperature of about 24° C. and has the composition:
Acetic Acid: Trace;
Hydrogen Chloride: 94.18 Percent;
Acetyl Chloride: Nil;
Chlorine: Balance.

This gas is led to a suitable hydrogen chloride recovery system.

The acetic acid liquid collected from the bottom of the column C-3 contains about 99.28% of acetic acid and 0.72% of acetyl chloride and is delivered through line 50 to be mixed with incoming acetyl chloride and acetic acid of line 16 as discussed above.

Gaseous chlorine fed to the reactor R-1 through line 20 generally is proportioned to ensure introduction of a small amount of unreacted chlorine in the off gas coming from line 48 and to ensure a good selectivity of monochloroacetic acid with low polychloroacetic acids production. Preferably, the amount of chlorine is in the range of 65 to 85 mol percent of the theoretical amount required to react with the acetic acid to produce monochloroacetic acid. That is, about 0.65 to 0.85 moles of chlorine is fed per mole of acetic acid fed to the Reactor R-1. While higher proportions of chlorine, rarely in excess of one mole per mol of acetic acid, may be used, this increased proportion tends to increase polychloro derivatives produced.

Acetic anhydride is fed largely to compensate for loss of acetyl chloride, some quantity of acetyl chloride usually being in the off gas escaping to line 48. This line delivers the gases to a system for hydrogen chloride and chlorine absorption and recovery. In any event, the better the recovery of acetyl chloride, the lower the amount of acetic anhydride is required.

The acetic acid used is anhydrous or substantially so, rarely containing more than five percent by weight of water and generally having a water content not over about 2 or 3%, preferably being anhydrous. The acetic anhydride added may be partially consumed removing water in the other reactants. Accordingly, the hydrogen chloride and the monochloroacetic acid produced as well as the acetic acid-acetyl chloride mixture leaving column C-1 through line 16 are substantially anhydrous.

Some variation is possible in the composition of the respective streams illustrated in the drawing and as discussed above may be conducted without departure from the spirit of the invention. For example, as the temperature within column C-1 is raised, some increase may occur in the acetyl chloride and acetic acid content of the gas in line 36. In that case, greater care is required to scrub these out with cold acetic acid in column C-3 and/or to condense acetyl chloride and acetic acid in condenser 37 and to recycle the condensate to the reactor.

Also, some acetic acid is stripped along with acetyl chloride from the hot liquid phase entering column C-2 by the hydrogen chloride passing upward therein. The gas or vapor escaping through line 44 which has a temperature of about 90° C. is cooled below 35° C. for example, to 15° C. or below in condenser 39 and this condenses the acetic acid therefrom. The condensed acetic acid is returned to one of the reactors or to line 12 and the cooled gas is forwarded to the lower part of column C-3.

The temperature in the reactors R-1, R-2 and R-3 may be higher or lower than 110° C., generally above about 75° to 150° C., but rarely above 125° C.

The time of retention of reactants in the reactors should be sufficient to achieve substantial conversion (more than 50%) of the acetic acid to monochloroacetic acid. The exact length of time depends upon reaction temperature but generally is in the range of 1 to 12 hours.

It will be noted that acetic acid is supplied to the reactor in two streams (lines 16 and 50). The amounts thereof in these respective streams are proportioned to hold the acetyl chloride largely in solution in column C-1 and to recover all or at least an optimum amount of acetyl chloride from the gas stream passing through column C-3. This can be effective accomplished by feeding substantially equal amounts of acetic acid to each of the lines 12 and 52. However, it will be understood that these proportions may be varied to long as the general objectives are accomplished.

Some chlorine remains unabsorbed in the reactors in most cases. Therefore, the hydrogen chloride stream fed to column C-1 usually contains a small residue of elemental chlorine. Because of the lower temperature and high dilution, also perhaps because of the other conditions of gas-liquid contact (rate of gas flow-through, low solubility of chlorine etc.), little or no chlorine is absorbed or reacted in column C-1 as a general rule, and chlorination of acetic acid in column C-1 is minor if it occurs at all. Accordingly, the temperature easily may be held low because substantial heat evolution from exothermic chlorination is not encountered. Excessive temperature, of course, is objectionable not only because acetyl chloride enters the gaseous phase but also because thermal disassociation tends to reduce the conversion to acetyl chloride.

While the flow sheet illustrates a concurrent flow of the reactant of chlorine and acetic acid, the process may also be conducted counter currently, for example, by feeding chlorine into reactor R-3 and acetic acid into reactor R-1 while withdrawing gaseous hydrogen chloride from reactor R-1 and liquid reaction product from reactor R-3.

The various steps in the process may be conducted readily at or near atmospheric pressure; for example, 10 to 200 millimeters of mercury above atmospheric pressure. If desired, a slight vacuum may be imposed on the system or parts thereof such as in line 48 and other gaseous lines in order to reduce the risk of leaking fumes into the surrounding atmosphere.

Of course certain advantages may accrue if certain parts of the system such as column C-1, column C-3 or at least one of the reactors are at a superatmospheric pressure since vaporization of acetyl chloride may be reduced and chlorine absorption can be improved. However, in such a case, greater precaution must be taken to provide a tight well-gasketed system to avoid fume leakage.

It will be understood that as the conditions of operation are varied, the compositions of the respective gas and liquid phase also change within the scope of the invention.

Pure or substantially pure monochloroacetic acid (MCA) can be recovered from the crude product by cooling and crystallization of the monochloroacetic acid and draining and washing off the mother liquid.

One advantage of the process herein contemplated is that it does not require the presence of inorganic catalysts or inhibitors such as phosphorous trichloride, sulfates, phosphates, nitrates or acetates of cobalt, manganese, chromium, nickel, sodium, barium, lithium, or the like such as stannous chloride, chromic acetate, manganese acetate, etc. The presence of these agents complicate the problems of recovering pure monochloroacetic acid from the crude product produced by this process.

Although the present invention has been described with reference to specific details of certain embodiments thereof, it is not intended that such details shall be regarded as limitations upon the scope of the invention except insofaras included in the accompanying claims.

We claim:
1. A method of producing monochloroacetic acid which comprises:
   (a) chlorinating at a temperature of at least 75° C. a mixture of acetyl chloride and acetic acid to produce a gaseous fraction comprising hydrogen chloride gas and a liquid fraction comprising monochloroacetic acid and acetic acid and separating the hydrogen chloride gas from the liquid, (b) separately contacting resulting hydrogen chloride from Step (a) with a solution of acetic acid and acetic anhydride at a temperature not above 60° C. to form a liquid mixture of acetic acid and acetyl chloride and a second gaseous hydrogen chloride gas containing acetyl chloride, (c) contacting at least part of the second gaseous hydrogen chloride with the liquid from Step (a) to strip acetyl chloride from the liquid and produce a third gaseous hydrogen chloride fraction containing acetyl chloride, (d) scrubbing said third gaseous fraction with liquid acetic acid and feeding the resulting acetic acid-acetyl chloride solution to Step (a).

2. The method of claim 1 wherein the liquid mixture of Step (b) is fed to Step (a).

3. The method of claim 1 wherein the gaseous hydrogen chloride produced by Step (a) contains chlorine and wherein the amount of chlorine fed to Step (b) in said hydrogen chloride gas is small compared to the amount of chlorine fed to Step (a).

4. A continuous process of preparing monochloroacetic acid which comprises (a) forming a liquid mixture of acetic acid and acetyl chloride, (b) feeding chlorine to said mixture in a reactor while maintaining the resulting mixture at 75° to 150° C., (c) withdrawing liquid reaction mixture containing monochloracetic acid and gaseous hydrogen chloride from said reactor, (d) contacting separately said gaseous hydrogen chloride with a liquid mixture of acetic acid and acetic anhydride at a temperature not substantially in excess of 35° C. to generate acetyl chloride dissolved in said acetic acid and (e) feeding the resulting acetic acid-acetyl chloride mixture to (a).

5. The process of claim 4 wherein the liquid mixture and gaseous chlorine are progressively passed through a series of reactor zones maintained at 75° to 150° C.

* * * * *

UNITED STATES PATENT AND TRADEMARK OFFICE
CERTIFICATE OF CORRECTION

PATENT NO. : 4,281,184
DATED : July 28, 1981
INVENTOR(S) : PLACIDO SPAZIANTE ET AL.

It is certified that error appears in the above—identified patent and that said Letters Patent is hereby corrected as shown below:

Column 3, line 3: "of more" should read -- or more --.

Signed and Sealed this

Twenty-fourth Day of November 1981

[SEAL]

Attest:

GERALD J. MOSSINGHOFF

*Attesting Officer*  *Commissioner of Patents and Trademarks*